United States Patent

Hearsey

[11] 4,115,445
[45] Sep. 19, 1978

[54] PROCESS FOR THE PREPARATION OF TRISUBSTITUTED UREAS

[75] Inventor: Colin John Hearsey, Surbiton, England

[73] Assignee: Quimco GmbH, Zurich, Switzerland

[21] Appl. No.: 549,146

[22] Filed: Feb. 12, 1975

Related U.S. Application Data

[62] Division of Ser. No. 346,480, Mar. 30, 1973, Pat. No. 3,911,006.

[30] Foreign Application Priority Data

Apr. 5, 1972 [GB] United Kingdom ............... 15677/72
Apr. 18, 1972 [GB] United Kingdom ............... 17872/72
May 5, 1972 [GB] United Kingdom ............... 21063/72

[51] Int. Cl.$^2$ .......................................... C07C 127/15
[52] U.S. Cl. .......................... 260/553 A; 260/293.86; 260/326.11 R; 260/326.85; 260/453 R; 260/543 A; 544/165
[58] Field of Search ............ 260/553 A, 247.2 A, 260/287 R, 293.86, 326.11 R, 326.4, 326.85

[56] References Cited

U.S. PATENT DOCUMENTS

| | | | |
|---|---|---|---|
| 2,655,534 | 10/1953 | Searle | 260/553 A |
| 3,392,197 | 7/1968 | Swakon | 260/553 R |
| 3,539,587 | 11/1970 | Swakon | 260/553 R X |
| 3,636,104 | 1/1972 | Kober et al. | 260/552 R |
| 3,865,875 | 2/1975 | Hearsey et al. | 260/553 A |

FOREIGN PATENT DOCUMENTS

| | | | |
|---|---|---|---|
| 203,940 | 9/1955 | Australia | 260/553 A |
| 634,690 | 1/1962 | Canada | 260/553 A |
| 875,984 | 8/1961 | United Kingdom | 260/553 A |
| 1,431,654 | 4/1976 | United Kingdom | 260/553 A |
| 1,378,481 | 12/1974 | United Kingdom | 260/553 A |

OTHER PUBLICATIONS

Martin, CA 78: 97323d (1973).

Primary Examiner—Winston A. Douglas
Assistant Examiner—Thomas A. Waltz
Attorney, Agent, or Firm—Stevens, Davis, Miller & Mosher

[57] ABSTRACT

The present invention provides a process for preparing a trisubstituted urea of the general formula:

R(NHCONR'R'')$_n$ in which R is a substituted or unsubstituted mono-, di- or polyvalent aromatic radical, R' is a substituted or unsubstituted monovalent aliphatic or aromatic radical and R'' is a substituted or unsubstituted monovalent aliphatic radical or R' and R'' together represent a substituted or unsubstituted divalent radical in which at least one of the two carbon atoms adjoining the nitrogen atom of the urea is aliphatic, and $n$ is an integer, wherein an aromatic nitrocompound of the general formula:—R(NO$_2$)$_n$ or an aromatic nitrosocompound of the general formula:—R(NO)$_n$ is allowed to react with a secondary ammonium N,N-disubstituted thiolcarbamate of the general formula:

R'R''NCOS$^-$.NH$_2$$^+$R'R'' or with a mixture of a secondary amine of the general formula:—R'R''NH and carbon monoxide and sulphur, carbon monoxide and hydrogen sulphide, or carbonyl sulphide, or with a mixture of a secondary ammonium sulphide or hydrosulphide of the general formula:

(R'R''NH$_2$)$_2$$^+$S$^{2-}$ or

R'R''NH$_2$$^+$.SH$^-$ and carbon monoxide.

4 Claims, No Drawings

PROCESS FOR THE PREPARATION OF TRISUBSTITUTED UREAS

This is a division, of application Ser. No. 346,480, filed Mar. 30, 1973, now U.S. Pat. No. 3,911,006.

This invention relates to the preparation of trisubstituted ureas from aromatic nitrocompounds or from aromatic nitrosocompounds. The products have several important applications, particularly as agricultural chemicals and as intermediates in the synthesis of other important chemicals, including carbamates and isocyanates.

At the present time, aromatic trisubstituted ureas are most frequently prepared by reaction of an aromatic isocyanate with a secondary amine. The isocyanate will normally have been prepared by the reaction of phosgene with the corresponding primary amine, which is in turn likely to have been prepared by reduction of the corresponding nitrocompound. There are several undesirable features in this conventional method, not least of which are the toxicity and corrosive nature of phosgene and the formation of hydrogen chloride as by-product. Furthermore, certain aromatic amines are known to have harmful physiological properties and some are also prone to aerial oxidation in storage.

It has now been found that trisubstituted ureas may readily be prepared in one step from aromatic nitrocompounds or nitrosocompounds.

Thus, according to the present invention, there is provided a process for preparing a trisubstituted urea of the general formula:

$$R(NHCONR'R'')_n$$

in which R is a substituted or unsubstituted mono-, di- or polyvalent aromatic radical, R' is a substituted or unsubstituted monovalent aliphatic or aromatic radical and R'' is a substituted or unsubstituted monovalent aliphatic radical or R' and R'' together represent a substituted or unsubstituted divalent radical in which at least one of the two carbon atoms adjoining the nitrogen atom of the urea is aliphatic, and n is an integer, wherein an aromatic nitrocompound of the general formula:

$$R(NO_2)_n$$

or an aromatic nitrosocompound of the general formula:

$$R(NO)_n$$

is allowed to react with a secondary ammonium N,N-disubstituted thiolcarbamate of the general formula:

$$R'R''NCOS.^-NH_2^+R'R''$$

or with a mixture of a secondary amine of the general formula:

$$R'R''NH$$

and carbon monoxide and sulphur, carbon monoxide and hydrogen sulphide, or carbonyl sulphide, or with a mixture of a secondary ammonium sulphide or hydrosulphide of the general formula:

$$(R'R''NH_2)_2^+S^{2-}$$

or $$R'R''NH_2^{30}.SH^-$$

and carbon monoxide.

Typical but not limiting substituents in R are alkyl, alkoxy, heterocyclic, halogen; typical buut not limiting substituents in R' are alkyl, aryl and heterocyclic; and typical but not limiting substituents in R'' are aryl and heterocyclic. Typical but not limiting secondary amines in which R' and R'' together represent a divalent radical in which at least one of the two carbon atoms adjoining the nitrogen atom is aliphatic are pyrrolidine, morpholine, piperidine and indoline.

It is to be understood that included in the definition of R above are heterocyclic radicals of aromatic nature.

When the starting material is $R(NO_2)_n$ it is believed that the present invention may be represented in general by the following equations:

$$R(NO_2)_n + 3nR'R''NCOS.^-NH_2^+R'R'' \rightarrow$$
$$R(NHCONR'R'')_n + 5nR'R''NH + 2nCO_2 + 3nS$$

$$R(NO_2)_n + 3nCO + nR'R''NH \rightarrow$$
$$R(NHCONR'R'')_n + 2nCO_2$$

$$R(NO_2)_n + 3nCOS + nR'R''NH \rightarrow$$
$$R(NHCONR'R'')_n + 2nCO_2 + 3nS$$

$$R(NO_2)_n + nCO + 2nH_2S + nR'R''NH \rightarrow$$
$$R(NHCONR'R'')_n + 2nH_2O + 2nS$$

$$2R(NO_2)_n + 5nCO + n(R'R''NH_2)_2^+S^{2-} \rightarrow$$
$$2R(NHCONR'R'')_n + 3nCO_2 + nS + nH_2O$$

Examples of trisubstituted ureas which may be prepared by the process of the present invention are 1,1-dimethyl-3-phenylurea, 1-m-chlorophenyl-3,3-dimethylurea, 1,1-dimethyl-3-(1-naphthyl)urea, 1,1-dimethyl-3-(5-quinolyl)urea, 1,1-diallyl-3-m-tolylurea, 1,1-(1,4-butylene)-3-m-chlorophenylurea, 1,1-dimethyl-3-p-tolylurea, 1,1-dimethyl-3-p-morpholinophenylurea, 1,1'-(2,4-tolylene)-bis-3,3-dimethylurea, 1,1'-(methylenedi-p-phenylene)-bis-3,3-dimethylurea, 1,1'-(ethylenedi-p-phenylene)-bis-3,3-diethylurea.

The reaction temperature is normally selected within the range 80°–200° C and the reaction is normally performed in an inert solvent. Typical of the solvents which may be used are benzene, toluene, chlorobenzene, xylene and o-dichlorobenzene.

In general, the highest yields are obtained when an aromatic nitrocompound is allowed to react with a secondary ammonium N,N-disubstituted thiolcarbamate. The latter reactant may conveniently be prepared and purified by the method described in a co-pending patent application U.S. patent application Ser. No. 312,750, now U.S. Pat. No. 3,865,875 by allowing the selected secondary amine in a suitable solvent to react with sulphur and carbon monoxide at a pressure between 5 and 60 atmospheres and at a temperature between 40° C and 100° C and by distilling the reaction products to obtain as distillate a purified mixture of reactant plus solvent.

Complete conversion of one equivalent of nitrocompound is achieved only when a minimum of three equivalents of thiolcarbamate salt is allowed to react with it. The rate of conversion is dependent on the nature of the nitrocompound. For example, the reaction of m- chloronitrobenzene with dimethylammonium N,N-dimethylthiolcarbamate in chlorobenzene under reflux conditions is virtually complete within 3 hours, whereas no detectable reaction takes place within 5 hours between p-dimethylaminonitrobenzene and dimethylammonium N,N-dimethylthiolcarbamate under the same conditions. In general, the faster is the rate of conversion, the higher is the yield.

The trisubstituted ureas formed by practising the present invention may be isolated by any one of several methods. In one of these the reaction products are distilled to remove volatiles and the residue is extracted with warm methanol. The methanol is then filtered to remove the insoluble sulphur and the methanol is distilled from the filtrate. The residue is extracted with refluxing benzene and filtered hot. The resulting solution is then cooled to give the required product as a precipitate.

Besides being important end-products, particularly as agricultural chemicals, trisubstituted ureas may readily be converted in a single step into isocyanates or carbamates by the methods described in two co-pending patent applications U.S. patent application Ser. Nos. 258,308 and 312,752 which are now respectively U.S. Pat. Nos. 3,898,259 and 3,873,553. Thus the present invention facilitates the preparation of a range of important materials whose manufacture conventionally involves the use of phosgene and the evolution of hydrogen chloride as a by-product. The by-products resulting from the practice of the present invention are carbon dioxide, sulphur and secondary amine (plus water in two of the less important modifications), of which the sulphur and the secondary amine may be recycled as such. The sulphur is recovered quantitatively at 100% conversion of starting material and at conversions of less than 100% the yield of sulphur may be used to estimate the conversion.

The present invention avoids the necessity to use aromatic amines as intermediates in the preparation of the title compounds, and also in the preparation of corresponding isocyanates and carbamates. This is an important advantage since several aromatic amines, such as 1-naphthylamine, have been shown to possess pronounced carcinogenic activity.

The process of the present invention is, in effect, a carbonylation of a nitro- or nitrosocompound. Many patents have been granted which relate to carbonylation reactions leading directly to carbamates or isocyanates. However, these methods invariably suffer from the disadvantage of requiring an expensive transitional metal catalyst, the recovery of which presents problems, and further of requiring, especially in the most high-yielding processes, the maintenance of a high carbon monoxide pressure for extended periods of time. Many of the best carbonylation processes using transition metal catalysts give carbamates rather than isocyanates, and the conversion of carbamates to isocyanates is known to be an unsatisfactory procedure. It follows that the present invention possesses several important advantages in terms both of cost and of versatility over carbonylation processes which use transition metal catalysts.

Certain substituents, such as p-chloro, chloromethyl and amino, in aromatic nitrocompounds are themselves reactive in the conditions of the present invention, and in these cases separate reactions proceed at sites other than the nitro group, thereby altering the constitution of the aromatic radical. If it is required to prepare trisubstituted ureas which possess o- and/or p-chloro substituents in the aromatic radical, it is possible to insert these substituents, using the method described in a co-pending patent application British Provisional Application No. 6494/73 by chlorination of the aromatic radical after conversion of the corresponding nitrocompound to the trisubstituted urea.

The following examples are given for the purpose of illustrating the present invention.

EXAMPLE 1

Nitrobenzene (5.0 g.) was allowed to react with dimethylammonium N,N-dimethylthiolcarbamate (33 g.) in chlorobenzene (42 g.) for 5 hours under reflux. At the end of this period, the volatiles, including some unreacted nitrobenzene, were distilled off and the residue was extracted with hot methanol. After filtration to remove sulphur (3.6 g., 92% of theoretical), the methanol was distilled off and the residue was dissolved in hot benzene and allowed to cool to give a precipitate of 1,1-dimethyl-3-phenylurea (4.0 g.; melting point 125°-128° C). A further 1.2 g. of product was obtained after the addition of 60-80 petroleum ether and this was recrystallised from benzene to give an additional 0.8 g. of 1,1-dimethyl-3-phenylurea, bringing the total yield to 86% related to a conversion of 92%.

EXAMPLE 2 m-Nitrotoluene (5.0 g.) was allowed to react with dimethylammonium N,N-dimethylthiolcarbamate (29 g.) in chlorobenzene (36 g.) for 17 hours under reflux. At the end of this period, the volatiles were distilled off and the residue was extracted with hot methanol. After filtration to remove sulphur (3.4 g., 97% of theoretical), the methanol was distilled off and the residue was dissolved in hot benzene and allowed to cool to give a precipitate of 1,1-dimethyl-3-m-tolylurea (3.2 g.; melting point 124°-127° C). A further 1.5 g. was obtained after the addition of 60-80 petroleum ether, bringing the total yield to 74% related to a conversion of 97%.

EXAMPLE 3 m-Chloronitrobenzene (12.8 g.) was allowed to react with dimethylammonium N,N-dimethylthiolcarbamate (66 g.) in chlorobenzene (84 g.) for 4¼ hours under reflux. At the end of this period, the volatiles were distilled off and the residue was extracted with hot methanol. After filtration to remove sulphur (7.8 g., 100% of theoretical), the methanol was distilled off and the residue was dissolved in hot benzene. Petroleum ether (60-80) was added and the solution was cooled to give a precipitate of 1-m-chlorophenyl-3,3-dimethylurea (14.4 g.; melting point 138°-142° C.) in 89% yield related to a conversion of 100%.

EXAMPLE 4 m-Chloronitrobenzene (3.0 g.) was allowed to react with diethylammonium N,N-diethylthiolcarbamate (20 g.) in chlorobenzene (20 g.) for 5 hours under reflux. At the end of this period, the volatiles were distilled off and the residue was extracted with hot methanol. After filtration to remove sulphur (1.4 g., 78% of theoretical), the methanol was distilled off and the residue was extracted with hot benzene and filtered hot. The benzene was then distilled from the filtrate and the residue was crystallised from 60-80 petroleum ether to give 1-m-chlorophenyl-3,3-diethylurea (2.2 g.; melting point 81°–82° C.) in 65% yield related to a conversion of 78%.

EXAMPLE 5

Nitrobenzene (5.0 g.) was allowed to react with dimethylammonium N,N-dimethylthiolcarbamate (18 g.) in chlorobenzene (24 g.) for 6 hours under reflux. At the end of this period, the reaction products were separated according to the method described in Example 1 to give sulphur (2.6 g., 67% of theoretical) and 1,1-dimethyl-3-phenylurea (3.8 g.) in 85% yield related to a conversion of 67%.

EXAMPLE 6

Nitrobenzene (5.5 g.) was allowed to react with dimethylammonium N,N-dimethylthiolcarbamate (40 g.) in o-dichlorobenzene (47 g.) for 14½ hours under reflux. At the end of this period, the reaction products were separated according to the method of Example 1 to give sulphur (4.3 g., 100% of theoretical) and 1,1-dimethyl-3-phenylurea (6.1 g.) in 84% yield related to a conversion of 100%.

EXAMPLE 7

Nitrosobenzene (5.0 g.) was allowed to react with dimethylammonium N,N-dimethylthiolcarbamate (50 g.) in o-dichlorobenzene (100 g.) for 7 hours under reflux. At the end of this period, the volatiles were distilled off and the residue was extracted with hot methanol. After filtration to remove sulphur (0.7 g., 23% of theoretical), the methanol was distilled off and the residue was dissolved in hot benzene. A small amount (about 10%) of 40–60 petroleum ether was added and the mixture was cooled, precipitating a tarry product. The mother liquor was poured off, more 40–60 petroleum ether was added and the solution was cooled further to give a precipitate of 1,1-dimethyl-3-phenylurea (0.5 g.) in 28% yield related to a conversion of 23%.

EXAMPLE 8

A ½-liter capacity autoclave was charged with nitrobenzene (50.0 g.), sulphur (16 g.), dimethylamine (45 g.), benzene (75 g.) and carbon monoxide to a pressure of 40 atmospheres. The contents of the autoclave were then heated to 110° C and retained within the range 110° C –140° C with stirring for 2 hours. The pressure of carbon monoxide was renewed to 40 atmospheres at intervals as required by passing in additional carbon monoxide. At the end of this period, the autoclave was allowed to cool below 70° C and the contents were removed and distilled to separate the volatiles. The latter included 10.3 g. of nitrobenzene, indicating a conversion of 79%. The residue was extracted with hot methanol and filtered to remove sulphur. The methanol was then distilled from the filtrate and the residue was dissolved in hot benzene. Petroleum ether (60–80) was added and the mixture was cooled to give a precipitate of crude 1,1-dimethyl-3-phenylurea (35.3 g.). Recrystallization of this product from water gave 27.6 g. of 1,1-dimethyl-3-phenylurea (melting point 127°–131° C), representing a yield of 52% related to a conversion of 79%.

EXAMPLE 9

A ½-liter autoclave was charged with nitrobenzene (30.0 g.), dimethylammonium sulphide (40 g.) benzene (60 g.) and carbon monoxide to a pressure of 50 atmospheres. The temperature of the autoclave was raised to 110° C and its contents were maintained at this temperature with stirring for 2½ hours. The pressure was renewed to 50 atmospheres at intervals as required by passing in more carbon monoxide. The contents of the autoclave were then allowed to cool below 70° C before being removed and distilled to separate the volatiles, which included unreacted nitrobenzene. The residue, weighing 16 g., was recrystallised from a mixture of benzene and 60–80 petroleum ether to give 1,1-dimethyl-3-phenylurea (12.3 g.).

EXAMPLE 10 o-Nitrotoluene (5.0 g.) was allowed to react with dimethylammonium N,N-dimethylthiolcarbamate (29 g.) in chlorobenzene (36 g.) for 17 hours under reflux. At the end of this period, the volatiles were distilled off and the residue was extracted with hot methanol. After filtration to remove sulphur (3.3 g., 94% of theoretical), the methanol was distilled off and the residue was dissolved in hot benzene and allowed to cool to give a precipitate of 1,1-dimethyl-3-o-tolylurea (4.1 g.; melting point 139°–143° C). A further 1.0 g. of product was obtained after the addition of a small amount of 60–80 petroleum ether and this was recrystallised from benzene to give an additional 0.7 g. of 1,1-dimethyl-3-o-tolylurea, bringing the total yield to 79% related to a conversion of 94%.

EXAMPLE 11 p-Nitrotoluene (5.0 g.) was allowed to react with dimethylammonium N,N-dimethylthiolcarbamate (29 g.) in chlorobenzene (36 g.) for 16 hours under reflux. At the end of this period, the reaction products were separated according to the method of Example 10 to give sulphur (1.8 g., 51% of theoretical) and 1,1-dimethyl-3-p-tolylurea (2.7 g.; melting point 154°–157° C) in 81% yield related to a conversion of 51%.

EXAMPLE 12

2,4-Dinitrotoluene (5.0 g.) was allowed to react with dimethylammonium N,N-dimethylthiolcarbamate (66 g.) in chlorobenzene (84 g.) for 17 hours under reflux. At the end of this period, the reaction products were separated according to the method of Example 10 to give sulphur (4.9 g., 93% of theoretical) and 6.5 g. of a product which after two further recrystallisations from benzene gave 1,1'-(2,4-tolylene)bis-3,3-dimethylurea (3.4 g.; melting point 182°–185° C) in 51% yield related to a conversion of 93%.

EXAMPLE 13

1-Nitronaphthalene (5.0 g.) was allowed to react with dimethylammonium N,N-dimethylthiolcarbamate (22 g.) in chlorobenzene (28 g.) for 14½ hours under reflux. At the end of this period, the reaction products were separated according to the method of Example 10 to give sulphur (2.8 g., 100% of theoretical) and 1,1-dimethyl-3-(1-naphthyl)urea (3.1 g.; melting point 164°–158° C) in 50% yield related to a conversion of 100%.

EXAMPLE 14

5-Nitroquinoline (4.3 g.) was allowed to react with dimethylammonium N,N-dimethylthiolcarbamate (33 g.) in chlorobenzene (43 g.) for 17 hours under reflux. At the end of this period, the reaction products were separated according to the method of Example 10 to give sulphur (2.1 g., 89% of theoretical) and crude 1,1- dimethyl-3-(5-quinolyl)urea (3.3 g.). Further recrystallisation from a mixture of methanol and water gave 2.2 g. of 1,1-dimethyl-3-(5-quinolyl)urea with melting point 188°-193° C, representing a 47% yield related to a conversion of 89%.

EXAMPLE 15 p-Morpholinonitrobenzene (5.0 g.) was allowed to react with dimethylammonium N,N-dimethylthiolcarbamate (26 g.) in chlorobenzene (34 g.) of 18¼ hours under reflux. At the end of this period, the reaction products were separated according to the method of Example 10 to give sulphur (0.6 g., 30% of theoretical) and 1.0 g. of crude product, which on further recrystallisation from benzene gave 1,1-dimethyl-3-p-morpholinophenylurea (0.6 g.; melting point 199°-204° C) in 33% yield related to a conversion of 30%.

EXAMPLE 16

2-Nitrobiphenyl (5.0 g.) was allowed to react with dimethylammonium N,N-dimethylthiolcarbamate (33 g.) in chlorobenzene (117 g.) for 16 hours under reflux. At the end of this period, the volatiles were distilled off and the residue was extracted with hot methanol. After filtration to remove sulphur (1.8 g.; 75% of theoretical), the methanol was distilled off and the residue was extracted with hot benzene and filtered hot. Petroleum ether (40–60) was added to the filtrate, which was then cooled to give 3.4 g. of crude product. Recrystallisation from a mixture of benzene and petroleum ether gave 1-(2-biphenyl)-3,3-dimethylurea (2.3 g.; melting point 89°-93° C) in 51% yield related to a conversion of 75%.

What is claimed is:

1. A one-step process for preparing a trisubstituted urea of the formula

R(NHCONR'R")$_n$ which comprises reacting a compound having the formula which comprises reacting a compound having the formula R(NO$_2$)$_n$ with a secondary amine of the formula

R'R"NH and carbon monoxide and sulfur or carbonyl sulfide at super atmospheric pressure in an inert solvent at a temperature within the range 80°-200° C., wherein R is an unsubstituted mono, di- or polyvalent aromatic radical or is substituted only with groups which are nonreactive under the reaction conditions, R' and R" are monovalent aliphatic radicals or R' and R" together represent a divalent aliphatic radical, and n is an integer.

2. The process of claim 1 wherein n = 1.

3. The process of claim 2 wherein the nitrocompound and diamine are reacted with sulfur and carbon monoxide.

4. The process of claim 2 wherein dimethyl amine and nitrobenzene are reacted with sulfur and carbon monoxide.

* * * * *